(12) United States Patent
Pathak

(10) Patent No.: US 7,323,189 B2
(45) Date of Patent: Jan. 29, 2008

(54) LIQUID AND LOW MELTING COATINGS FOR STENTS

(75) Inventor: Chandrashekhar Pathak, Austin, TX (US)

(73) Assignee: eV3 Peripheral, Inc., Plymouth, MN (US)

(*) Notice: Subject to any disclaimer, the term of this patent is extended or adjusted under 35 U.S.C. 154(b) by 405 days.

(21) Appl. No.: 10/027,374

(22) Filed: Dec. 21, 2001

(65) Prior Publication Data

US 2003/0083740 A1 May 1, 2003

Related U.S. Application Data

(63) Continuation-in-part of application No. 09/991,235, filed on Oct. 22, 2001, now abandoned.

(51) Int. Cl.
*A61F 2/02* (2006.01)

(52) U.S. Cl. .................................................. 424/423

(58) Field of Classification Search ................ 424/423
See application file for complete search history.

(56) References Cited

U.S. PATENT DOCUMENTS

| | | | |
|---|---|---|---|
| 4,768,507 A | 9/1988 | Fischell et al. ......... 128/303 R |
| 4,795,458 A | 1/1989 | Regan ........................... 623/1 |
| 4,952,419 A | 8/1990 | De Leon et al. |
| 5,015,253 A | 5/1991 | MacGregor ..................... 623/1 |
| 5,059,211 A | 10/1991 | Stack et al. .................. 606/198 |
| 5,135,516 A | 8/1992 | Sahtjian et al. ............. 604/264 |
| 5,163,952 A | 11/1992 | Froix ............................ 623/1 |
| 5,240,913 A | 8/1993 | Maraganore et al. ......... 514/13 |
| 5,258,020 A | 11/1993 | Froix ............................ 623/1 |
| 5,282,824 A | 2/1994 | Gianturco ................... 606/198 |
| 5,292,321 A | 3/1994 | Lee .............................. 606/28 |
| 5,292,331 A | 3/1994 | Boneau ..................... 606/198 |
| 5,304,121 A | 4/1994 | Sahatjian ..................... 604/53 |
| 5,314,688 A | 5/1994 | Kauffman et al. .......... 424/423 |
| 5,334,201 A | 8/1994 | Cowan ......................... 623/1 |
| 5,366,504 A | 11/1994 | Andersen et al. ............. 623/11 |
| 5,380,299 A | 1/1995 | Fernot et al. ................ 604/265 |
| 5,383,928 A | 1/1995 | Scott et al. .................... 623/1 |
| 5,405,378 A | 4/1995 | Strecker ........................ 623/1 |
| 5,411,550 A | 5/1995 | Herweck et al. ............... 623/1 |
| 5,419,760 A | 5/1995 | Narciso, Jr. .................... 604/8 |

(Continued)

FOREIGN PATENT DOCUMENTS

EP 0734721 * 3/1996

(Continued)

OTHER PUBLICATIONS

Auer, J. et al., "Clinical Significance of Pleiotropic Effects of Statins: Lipid Reduction and Beyond," *Current Medicinal Chemistry*, vol. 9, No. 20, pp. 1831-1850 (2002).

*Primary Examiner*—Carlos A. Azpuru
(74) *Attorney, Agent, or Firm*—Kudirka & Jobse, LLP

(57) ABSTRACT

A method for forming liquid coatings for medical devices such as stents and angioplasty balloons is provided. The liquid coatings can be made from biodegradable materials in liquid, low melting solid, or wax forms, which preferably degrade in the body without producing potentially harmful fragments. The liquid coatings may also contain biologically active components, which are released from the coatings through diffusion from the coatings and the degradation of the coatings.

23 Claims, 5 Drawing Sheets

U.S. PATENT DOCUMENTS

| | | | |
|---|---|---|---|
| 5,423,885 A | 6/1995 | Williams | 623/1 |
| 5,439,446 A | 8/1995 | Barry | 604/96 |
| 5,443,495 A | 8/1995 | Buscemi et al. | 623/1 |
| 5,449,382 A | 9/1995 | Dayton | 623/1 |
| 5,464,450 A | 11/1995 | Buscemi et al. | 623/6 |
| 5,464,650 A | 11/1995 | Berg et al. | 427/2.3 |
| 5,507,771 A | 4/1996 | Gianturco | 606/198 |
| 5,545,211 A | 8/1996 | An et al. | 623/1 |
| 5,545,213 A | 8/1996 | Keogh et al. | 623/1 |
| 5,550,013 A | 8/1996 | Chen et al. | 623/1 |
| 5,554,182 A | 9/1996 | Dinh et al. | 623/1 |
| 5,556,413 A | 9/1996 | Lam | 606/198 |
| 5,571,086 A | 11/1996 | Kaplan et al. | 604/96 |
| 5,571,166 A | 11/1996 | Dinh et al. | 623/1 |
| 5,575,815 A | 11/1996 | Slepian et al. | 623/1 |
| 5,578,075 A | 11/1996 | Dayton | 623/1 |
| 5,588,352 A | 12/1996 | Harrison | 99/339 |
| 5,591,199 A | 1/1997 | Porter et al. | 606/198 |
| 5,593,434 A | 1/1997 | Williams | 623/1 |
| 5,599,352 A | 2/1997 | Dinh et al. | 623/1 |
| 5,603,722 A | 2/1997 | Phan et al. | 606/198 |
| 5,605,696 A | 2/1997 | Eury et al. | 424/423 |
| 5,607,467 A | 3/1997 | Froix | 423/1 |
| 5,609,629 A | 3/1997 | Fearnot et al. | 623/1 |
| 5,622,188 A | 4/1997 | Plaia et al. | 128/898 |
| 5,624,411 A | 4/1997 | Tuch | 604/265 |
| 5,628,785 A | 5/1997 | Schwartz et al. | 623/1 |
| 5,629,077 A | 5/1997 | Turnlund et al. | 442/38 |
| 5,632,771 A | 5/1997 | Boatman et al. | 623/1 |
| 5,632,840 A | 5/1997 | Campbell | 156/196 |
| 5,637,113 A | 6/1997 | Tartaglia et al. | 623/1 |
| 5,649,977 A | 7/1997 | Campbell | 623/1 |
| 5,653,747 A | 8/1997 | Dereume | 623/1 |
| 5,670,161 A | 9/1997 | Healy et al. | 424/426 |
| 5,674,241 A | 10/1997 | Bley et al. | 606/198 |
| 5,674,242 A | 10/1997 | Phan et al. | 606/198 |
| 5,674,276 A | 10/1997 | Andersen et al. | 623/1 |
| 5,674,278 A | 10/1997 | Boneau | 623/1 |
| 5,674,287 A | 10/1997 | Slepian et al. | 623/11 |
| 5,700,286 A | 12/1997 | Tartaglia et al. | 623/1 |
| 5,713,949 A | 2/1998 | Jayaraman | 623/1 |
| 5,716,981 A | 2/1998 | Hunter et al. | 514/449 |
| 5,718,159 A | 2/1998 | Thompson | 87/33 |
| 5,718,713 A | 2/1998 | Frantzen | 606/198 |
| 5,725,549 A | 3/1998 | Lam | 606/198 |
| 5,728,751 A | 3/1998 | Patnaik | 523/112 |
| 5,733,327 A | 3/1998 | Igaki et al. | 623/1 |
| 5,766,710 A | 6/1998 | Turnlund et al. | 428/36.1 |
| 5,769,883 A | 6/1998 | Buscemi et al. | 623/1 |
| 5,772,629 A | 6/1998 | Kaplan | 604/52 |
| 5,772,668 A | 6/1998 | Summers et al. | 606/108 |
| 5,788,979 A | 8/1998 | Alt et al. | 424/426 |
| 5,797,887 A | 8/1998 | Rosen et al. | 604/265 |
| 5,800,538 A | 9/1998 | Slepian et al. | 623/11 |
| 5,824,045 A | 10/1998 | Alt | 623/1 |
| 5,824,049 A | 10/1998 | Ragheb et al. | 623/1 |
| 5,827,322 A | 10/1998 | Williams | 606/198 |
| 5,836,316 A | 11/1998 | Plaia et al. | 128/898 |
| 5,840,387 A | 11/1998 | Berlowitz-Tarrant et al. | 428/36.91 |
| 5,843,089 A | 12/1998 | Sahatjian et al. | 606/108 |
| 5,843,172 A | 12/1998 | Yan | 623/1 |
| 5,861,027 A | 1/1999 | Trapp | 623/1 |
| 5,871,538 A | 2/1999 | Dereume | 623/1 |
| 5,873,904 A | 2/1999 | Ragheb et al. | 623/1 |
| 5,876,433 A | 3/1999 | Lunn | 623/1 |
| 5,876,449 A | 3/1999 | Starck et al. | 623/12 |
| 5,879,382 A | 3/1999 | Boneau | 623/1 |
| 5,891,108 A | 4/1999 | Leone et al. | 604/264 |
| 5,891,196 A | 4/1999 | Lee et al. | 8/94.11 |
| 5,893,868 A | 4/1999 | Hanson et al. | 606/198 |
| 5,895,407 A | 4/1999 | Jayaraman | 606/198 |
| 5,900,246 A | 5/1999 | Lambert | 424/429 |
| 5,904,146 A | 5/1999 | Plaia et al. | 128/898 |
| 5,928,279 A | 7/1999 | Shannon et al. | 623/1 |
| 5,954,744 A | 9/1999 | Phan et al. | 606/198 |
| 5,968,093 A | 10/1999 | Kranz | 623/1 |
| 5,972,027 A | 10/1999 | Johnson | 623/1 |
| 5,976,155 A | 11/1999 | Foreman et al. | 606/108 |
| 5,976,169 A | 11/1999 | Imran | 606/194 |
| 5,980,551 A | 11/1999 | Summers et al. | 606/194 |
| 6,004,943 A | 12/1999 | Shi et al. | 514/44 |
| 6,010,530 A | 1/2000 | Goicoechea | 623/1 |
| 6,015,402 A | 1/2000 | Sahota | 604/523 |
| 6,015,430 A | 1/2000 | Wall | 623/1 |
| 6,019,789 A | 2/2000 | Dinh et al. | 623/1 |
| 6,033,434 A | 3/2000 | Borghi | 623/1 |
| 6,033,436 A | 3/2000 | Steinke et al. | 623/1 |
| 6,036,725 A | 3/2000 | Avellanet | 623/1 |
| 6,039,757 A | 3/2000 | Edwards et al. | 623/1 |
| 6,041,305 A | 3/2000 | Sakurai | 705/5 |
| 6,071,305 A | 6/2000 | Brown et al. | 623/1 |
| 6,077,298 A | 6/2000 | Tu et al. | 623/1.19 |
| 6,083,257 A | 7/2000 | Taylor et al. | 623/1 |
| 6,086,455 A | 7/2000 | Frantzen | 451/36 |
| 6,086,611 A | 7/2000 | Duffy et al. | 623/1 |
| 6,087,552 A | 7/2000 | Gregory | 623/11 |
| 6,090,134 A | 7/2000 | Tu et al. | 623/1 |
| 6,090,135 A | 7/2000 | Plaia et al. | 623/1.11 |
| 6,096,070 A | 8/2000 | Ragheb et al. | 623/1 |
| 6,099,561 A | 8/2000 | Alt | 623/1.44 |
| 6,099,562 A | 8/2000 | Ding et al. | 623/1.46 |
| 6,099,563 A | 8/2000 | Zhong | 623/1.46 |
| 6,100,443 A | 8/2000 | Sims et al. | 800/14 |
| 6,102,943 A | 8/2000 | McGuinness | 623/1.12 |
| 6,113,628 A | 9/2000 | Borghi | 623/1.016 |
| 6,120,523 A | 9/2000 | Crocker et al. | 606/192 |
| 6,120,535 A | 9/2000 | McDonald et al. | 623/1.39 |
| 6,120,536 A | 9/2000 | Ding et al. | 623/1.43 |
| 6,129,757 A | 10/2000 | Weadock | 623/1.39 |
| 6,133,242 A | 10/2000 | Zalewski et al. | 514/44 |
| 6,146,358 A | 11/2000 | Rowe | 604/103.02 |
| 6,149,681 A | 11/2000 | Houser et al. | 623/1.12 |
| 6,159,488 A | 12/2000 | Nagler et al. | 424/423 |
| 6,161,399 A | 12/2000 | Jayaraman | 66/170 |
| 6,165,209 A | 12/2000 | Patterson et al. | 623/1.1 |
| 6,168,619 B1 | 1/2001 | Dinh et al. | 623/1.13 |
| 6,171,232 B1 | 1/2001 | Papandreou et al. | 600/36 |
| 6,171,609 B1 | 1/2001 | Kunz | 424/422 |
| 6,174,326 B1 | 1/2001 | Kitaoka et al. | 623/1 |
| 6,174,329 B1 | 1/2001 | Callol et al. | 623/1.34 |
| 6,177,523 B1 | 1/2001 | Reich et al. | 525/459 |
| 6,183,353 B1 | 2/2001 | Frantzen | 451/104 |
| 6,187,035 B1 | 2/2001 | Jang | 623/1.15 |
| 6,193,746 B1 | 2/2001 | Strecker | 623/1.13 |
| 6,197,047 B1 | 3/2001 | Kranz | 623/1.15 |
| 6,197,051 B1 | 3/2001 | Zhong | 623/1.46 |
| 6,206,916 B1 | 3/2001 | Furst | 623/1.46 |
| 6,210,436 B1 | 4/2001 | Weadock | 623/1.39 |
| 6,214,040 B1 | 4/2001 | Jayaraman | 623/1.13 |
| 6,214,042 B1 | 4/2001 | Jacobsen et al. | 623/1.2 |
| 6,214,115 B1 | 4/2001 | Taylor et al. | 118/423 |
| 6,217,607 B1 | 4/2001 | Alt | 623/11 |
| 6,221,099 B1 | 4/2001 | Andersen et al. | 623/1.15 |
| 6,224,626 B1 | 5/2001 | Steinke | 623/1.16 |
| 6,231,600 B1 | 5/2001 | Zhong | 623/1.42 |
| 6,240,616 B1 | 6/2001 | Yan | 29/527.2 |
| 6,241,691 B1 | 6/2001 | Ferrera et al. | 600/585 |
| 6,245,104 B1 | 6/2001 | Alt | 623/1.46 |
| 6,245,760 B1 | 6/2001 | He et al. | 514/234.8 |
| 6,248,129 B1 | 6/2001 | Froix | 623/1.42 |
| 6,251,136 B1 | 6/2001 | Guruwaiya et al. | 623/1.46 |
| 6,251,142 B1 | 6/2001 | Bernacca et al. | 623/23.57 |
| 6,253,443 B1 | 7/2001 | Johnson | 29/557 |

| | | | |
|---|---|---|---|
| 6,254,627 B1 | 7/2001 | Freidberg | 623/1.11 |
| 6,254,632 B1 | 7/2001 | Wu et al. | 623/1.15 |
| 6,255,277 B1 | 7/2001 | Stamler et al. | 514/2 |
| 6,258,121 B1 | 7/2001 | Yang et al. | 623/1.46 |
| 6,263,880 B1 | 7/2001 | Parker et al. | 128/898 |
| 6,264,690 B1 | 7/2001 | Von Oepen | 623/1.3 |
| 6,273,913 B1 | 8/2001 | Wright et al. | 623/1.42 |
| 6,280,411 B1 | 8/2001 | Lennox | 604/103.05 |
| 6,290,719 B1 | 9/2001 | Garberoglio | 623/1 |
| 6,290,722 B1 | 9/2001 | Wang | 623/1.46 |
| 6,299,604 B1 | 10/2001 | Ragheb et al. | 604/265 |
| 6,306,165 B1 | 10/2001 | Patnaik et al. | 623/1.43 |
| 6,306,166 B1 | 10/2001 | Barry et al. | 623/1.46 |
| 6,315,794 B1 | 11/2001 | Richter | 623/1.34 |
| 6,325,821 B1 | 12/2001 | Gaschino et al. | 623/1.15 |
| 6,331,186 B1 | 12/2001 | Wang et al. | 623/1.11 |
| 6,331,527 B1 | 12/2001 | Parmacek et al. | 514/44 |
| 6,368,658 B1 | 4/2002 | Schwarz et al. | |
| 2001/0001128 A1 | 5/2001 | Holman et al. | 623/1.11 |
| 2001/0003161 A1 | 6/2001 | Vardi et al. | 623/1.11 |
| 2001/0007082 A1 | 7/2001 | Dusbabek et al. | 623/1.11 |
| 2001/0007083 A1 | 7/2001 | Roorda | 623/1.15 |
| 2001/0009982 A1 | 7/2001 | Ferrera et al. | 600/585 |
| 2001/0010014 A1 | 7/2001 | Trozera | 623/1.16 |
| 2001/0016726 A1 | 8/2001 | Dubrul et al. | 604/509 |
| 2001/0016770 A1 | 8/2001 | Allen et al. | 623/1.15 |
| 2001/0027340 A1 | 10/2001 | Wright et al. | 623/1.15 |
| 2001/0029351 A1 | 10/2001 | Falotico et al. | 604/103.02 |
| 2001/0032010 A1 | 10/2001 | Sandock | 623/1.15 |
| 2001/0032014 A1 | 10/2001 | Yang et al. | 623/1.15 |
| 2001/0037144 A1 | 11/2001 | Kim et al. | 623/1.15 |
| 2001/0037145 A1 | 11/2001 | Guruwaiya et al. | 623/1.15 |
| 2001/0041929 A1 | 11/2001 | Oepen | 623/1.15 |
| 2001/0044649 A1 | 11/2001 | Vallana et al. | 623/1.15 |
| 2001/0044650 A1 | 11/2001 | Simso et al. | 623/1.16 |
| 2001/0044651 A1 | 11/2001 | Steinke et al. | 623/1.16 |
| 2001/0044652 A1 | 11/2001 | Moore | 623/1.16 |
| 2001/0044655 A1 | 11/2001 | Patnaik et al. | 623/1.43 |
| 2001/0047202 A1 | 11/2001 | Slaikeu et al. | 623/1.46 |
| 2001/0053928 A1 | 12/2001 | Edelman et al. | 623/1.1 |
| 2001/0056299 A1 | 12/2001 | Thompson | 623/1.53 |
| 2002/0002353 A1 | 1/2002 | Michal et al. | 604/265 |
| 2002/0002396 A1 | 1/2002 | Fulkerson | 623/1.11 |
| 2002/0002398 A1 | 1/2002 | Voinov | 623/1.15 |
| 2002/0004678 A1 | 1/2002 | Easterling | 623/1.15 |
| 2002/0004679 A1 | 1/2002 | Eury et al. | 623/1.15 |
| 2002/0004680 A1 | 1/2002 | Plaia et al. | 623/1.23 |
| 2002/0005206 A1 | 1/2002 | Falotico et al. | 128/898 |
| 2002/0007209 A1 | 1/2002 | Scheerder et al. | 623/1.15 |
| 2002/0007213 A1 | 1/2002 | Falotico et al. | 623/1.21 |
| 2002/0007214 A1 | 1/2002 | Falotico | 623/1.21 |
| 2002/0007215 A1 | 1/2002 | Falotico et al. | 623/1.21 |
| 2002/0044654 A1 | 4/2002 | Maeda et al. | 380/43 |
| 2003/0125800 A1 | 7/2003 | Shulze et al. | |

FOREIGN PATENT DOCUMENTS

WO  WO00/62830  10/2000

* cited by examiner

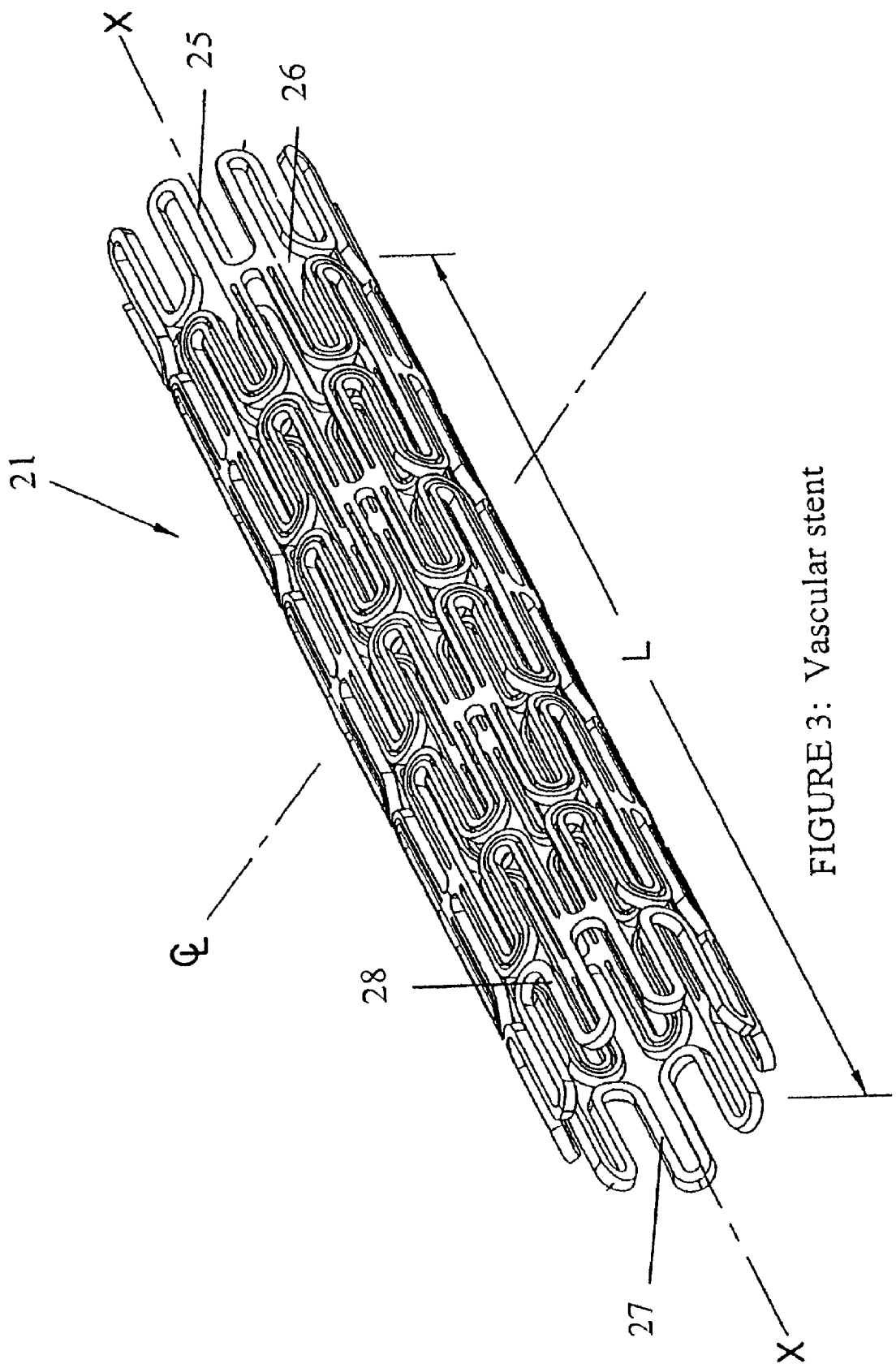
FIGURE 3: Vascular stent

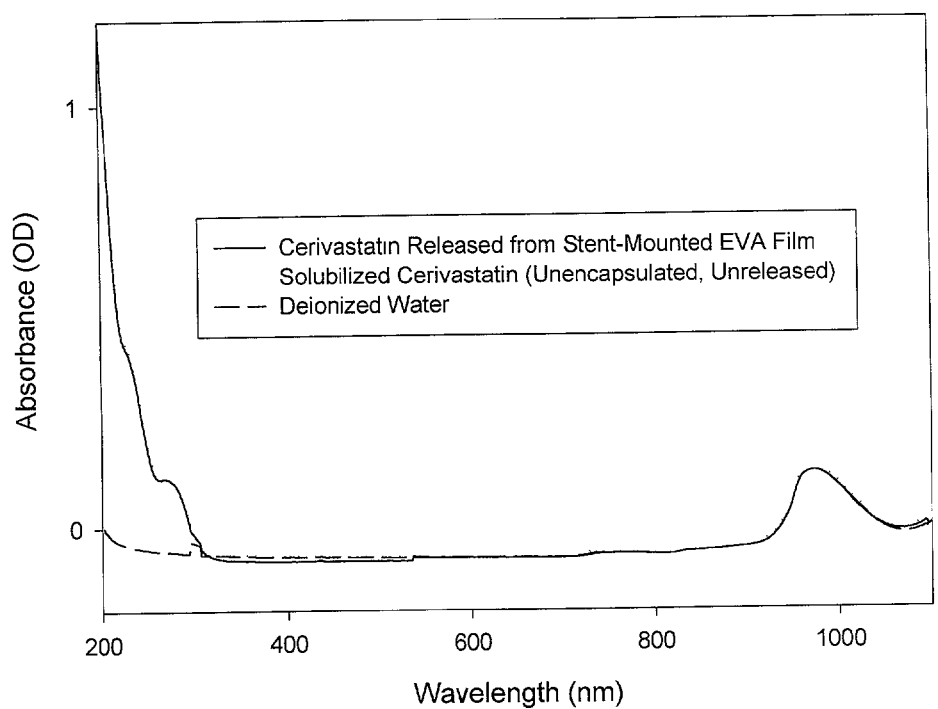
Figure 4: UV-VIS spectra comparison of cerivastatin released from EVA film and pure cerivastatin in deionized water

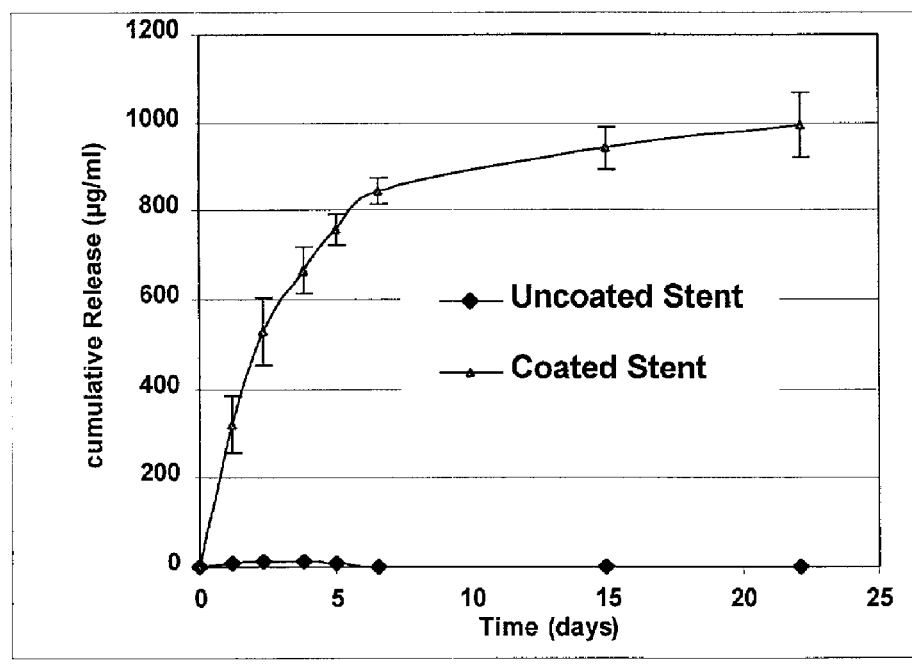
Figure 5: Cerivastatin release profile from EVA film wrapped on a stent Figure 6: Release of cerivastatin from liquid vitamin E carrier
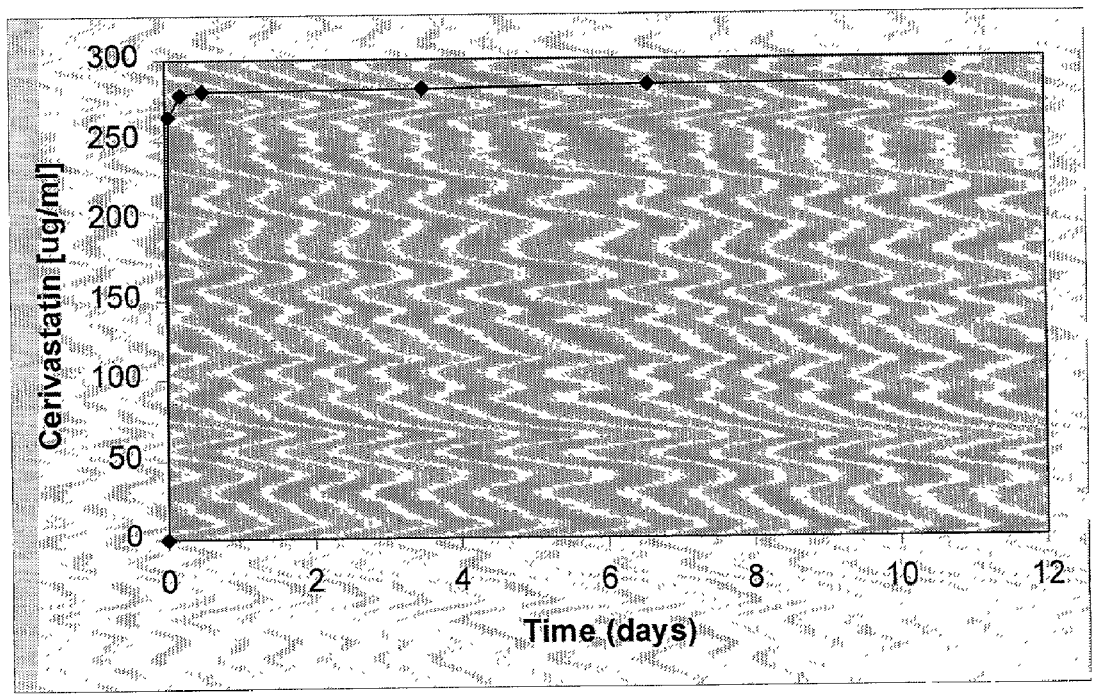

LIQUID AND LOW MELTING COATINGS FOR STENTS

CROSS-REFERENCE TO RELATED APPLICATIONS

This application is a continuation-in-part of U.S. patent application Ser. No. 09/991,235, filed Oct. 22, 2001 now abandoned, entitled "Stent Coatings Containing HMG-CoA Reductase Inhibitors," which is hereby incorporated herein by reference in its entirety.

BACKGROUND OF THE INVENTION

1. Field of the Invention

The present invention generally relates to coated stents, compositions for coating stents, methods of making coated stents, and methods of using coated stents.

2. Description of the Related Art

Stents are often used in the treatment of atherosclerosis, a disease of the vascular system in which arteries become partially, and sometimes completely, occluded with substances that may include lipids, cholesterol, calcium, and various types of cells, such as smooth muscle cells and platelets. Atherosclerosis is a very common disease which can be fatal, and methods of preventing the accumulation of occluding compounds in arteries are being investigated.

Percutaneous transluminal coronary angioplasty (PTCA) is a commonly used procedure to break up and/or remove already formed deposits along arterial walls. PTCA can also be used to treat vascular occlusions not associated with atherosclerosis. During PTCA, a catheter is threaded through a patient's arteries until the occluded area to be treated is reached. A balloon attached to the end of the catheter is then inflated at the occluded site. The expanded balloon breaks up the mass of occluding substances, resulting in a more open arterial lumen. However, there is a risk that the artery may re-close within a period of from one day to approximately six months after the procedure. This re-closure is known as restenosis. Accordingly, a balloon-only angioplasty procedure often does not result in a permanently reopened artery. To prevent restenosis, scaffolding devices called stents are often deployed in the lumen of the artery as a structural support to maintain the lumen in an open state. Unlike the balloon and the catheter used in an angioplasty procedure, the stent remains in the artery as a permanent prosthesis. Although technically feasible, removal of the stent from the artery is generally avoided.

Stents are typically elongated structures used to keep open lumens (i.e., openings) found in various parts of the body. Stents are usually implanted by coupling them in a compressed state to a catheter which is routed through the body to the site of stent deployment. The stent can be expanded to a size, which enables it to keep the lumen open by direct contact with the wall of the lumen once it is positioned at the desired site.

Blood vessels are common sites of stent deployment. Vascular stents are frequently used in blood vessels to open the vessel and provide improved blood flow. The stents are typically hollow, cylindrical structures made from struts or interconnected filaments. Vascular stents can be collapsed to a reduced diameter so that the stent can be guided through a patient's arteries or veins to reach the site of deployment. Stents are typically either coupled to the outside of the balloon for expansion by direct contact with the expanding balloon or are self-expanding upon removal of a restraint such as a wire or sleeve maintaining the stent in its collapsed state.

The stent is allowed to expand at the desired site to a diameter large enough to keep the blood vessel open. Vascular stents are often made of metal to provide the strength necessary to support the occluded arterial walls. Two of the preferred metals are Nitinol alloys of nickel and titanium, and stainless steel. Other materials that can be used in stents are ceramics, polymers, and plastics. Stents may be coated with a substance, such as a biodegradable or biostable polymer, to improve the biocompatibility of the stent, making it less likely to cause an allergic or other immunological response in a patient. A coating substance may also add to the strength of the stent. Some known coating substances include organic acids, their derivatives, and synthetic polymers that are either biodegradable or biostable. Biodegradable coating substances can degrade in the body; biostable coating substances do not. A problem with known biodegradable and biostable stent coatings is that both types of coatings are susceptible to breaking and cracking during the temperature changes and expansion/contraction cycles experienced during stent fabrication and use.

Stents located within a lumen in the body may not always prevent partial or complete restenosis. In particular, stents do not always prevent the re-narrowing of an artery following PTCA. In fact, the introduction and presence of the stent itself in the artery or vein can create regions of trauma such as, e.g., tears in the inner lining of the artery, called the endothelium. It is believed that such trauma can trigger migration of vascular smooth muscle cells, which are usually separated from the arterial lumen by the endothelium, into the arterial lumen, where they proliferate to create a mass of cells, which may in a matter of days or weeks re-occlude the artery. The resulting re-occlusion of the artery, which is sometimes seen after PTCA, is an example of restenosis. Coating a stent with a substance to make the surface of the stent smoother and to minimize damage to the endothelium has been one method used to create stents that are less likely to contribute to restenosis.

Currently, drug therapy for restenosis primarily consists of the systemic administration of drugs. However, delivering drugs in this manner may result in undesirable side effects in other areas of the body unrelated to the vascular occlusion. Also a drug which is delivered systemically is less effective in achieving the desired effect in the local area of the body in which it is actually needed. For example, an anti-restenosis drug delivered systemically may be sequestered or metabolized by other parts of the body, resulting in only a small amount of the drug reaching the local area where it is needed.

Stents with bioactive compounds or drugs in or on their coatings have been proposed. Typically, such coatings comprise a polymeric carrier and an active drug or anti-restenosis agent. One class of drugs that can be used in stent coatings is restenosis inhibitors. Although a number of drugs have been shown to be candidates to reduce restenosis rates in cardiovascular stents, there remains a need for coatings which can be shown to actually release the restenosis inhibiting compounds in their active forms. Further, there is a need for carriers for use in coated stents, which can carry drugs and release them in a sufficient concentration to produce the desired effect. In particular, there is a need for such stents, which can inhibit restenosis.

One problem with the biodegradable carriers currently proposed for incorporation in coatings for stents and angioplasty balloons is that, because they are invariably solids at body temperature and below, they may degrade into fragments which can be sharp. These fragments can damage the endothelium, and thus contribute to restenosis. There is thus a need for stents (and other medical devices such as angioplasty balloons) having biodegradable coatings, and particularly carriers used in such coatings, that do not break down into harmful fragments. Furthermore, there is a need for such coatings which contain bioactive compounds that can be released a carrier to provide localized drug delivery at the site of the stent. Coatings which can release a high dose of bioactive compound quickly, and thus prevent or treat an unhealthy condition as quickly as possible, are also desired.

SUMMARY OF INVENTION

Broadly, the invention relates to coated stents, methods of making coated stents and methods of using coated stents. At least certain embodiments of the invention provide a coated stent comprising a stent having a coating composition that includes a biologically active component and a biodegradable, low-melting carrier component. Accordingly, in one embodiment, the invention provides a stent having a coating composition comprising a biologically active component and a biodegradable carrier having a melting point of about 50° C. or less, more preferably about 45° C. or less. More particularly, the biodegradable carrier component has a melting point of from about 10° C. to about 50° C., more preferably from about 35° C. to about 45° C. In other specific embodiments, the invention provides a coated stent comprising a stent and a coating composition that includes a bioactive component and a biodegradable liquid carrier component having a viscosity of from about 0.1 to about 15,000 centipoise, and more preferably from about 0.1 to 5000 centipoise (cP). In yet another specific embodiment, the invention includes a stent with a coating composition that is in a solid state at room temperature (22° C.) outside a human body and that melts to form a liquid inside a human body.

Coating compositions according to the present invention are preferably hydrophobic. More preferably, the biodegradable carrier component of the coating composition is hydrophobic. The carrier component is also preferably biocompatible. The biodegradable carrier may comprise a polymer. When the biodegradable carrier comprises a polymer, the polymer preferably has a molecular weight of 50,000 or less, more preferably 5000 or less, and even more preferably 2000 or less. The carrier polymer may be selected from the group consisting of polyhydroxy acids, polyanhydrides, polyphosphazenes, biodegradable polyamides, polyalkylene oxalates, polyorthoesters, polyphosphoesters, polyorthocarbonates, and blends or copolymers thereof. Alternatively, and more preferably, the carrier comprises a non-polymer and is preferably entirely non-polymeric. For example, the carrier component may comprise vitamin E or its derivatives, oleic acid, peanut oil, or cottonseed oil, alone or in combination.

Preferably, the biologically active component is capable of inhibiting restenosis. The biologically active component may be selected from the group consisting of paclitaxel, actinomycin D, rapamycin, cerivastatin and other statin drugs. Preferably, those components are released from a stent in an amount effective to inhibit restenosis.

In certain specific embodiments, the coated stent comprises a stent and a coating composition comprising a biodegradable or biostable carrier component. Where the biodegradable or biostable carrier is itself a biologically active component, the carrier should have a melting point of about 50° C. or less.

In another aspect, the invention can include a method of coating a stent. A specific embodiment of the method includes providing a coating composition that includes a biologically active component and a biodegradable carrier component that has a melting point of about 50° C. or less, and applying the coating composition to the stent. In another specific embodiment, the invention includes a method that comprises providing a coating composition that includes a biologically active component and a biodegradable carrier component which has a viscosity of from about 0.1 to about 15,000 cP, and applying the coating composition to the stent.

In another embodiment, a method of coating a stent may comprise expanding the stent to an expanded position before applying the coating composition to the stent. The coating composition may be applied to the stent in any number of ways, e.g., by spraying the coating composition onto the stent, by immersing the stent in the coating composition, or by painting the stent with the coating composition. Other coating methods such as electrodeposition can also be used. In one embodiment, excess coating composition is allowed to drain from the stent. In another embodiment, the stent is dried after the coating composition is applied to the stent to provide a solid coating composition. In preferred embodiments, the coating is applied with the bioactive component dissolved in the carrier component. In alternative embodiments, the carrier component may be applied to the stent and the bioactive component applied to the carrier. In another alternative embodiment, the bioactive component may be applied to the stent and the carrier component applied to the bioactive component.

In one or more specific embodiments, the invention can include a treatment method, comprising inserting a coated stent into a body lumen of a person, the coated stent comprising a stent and a coating composition comprising a biodegradable carrier component and a biologically active component, the biodegradable carrier component having a melting point of about 50° C. or less, more preferably 45° C. or less. In other specific embodiments, the coated stent provides a stent and a coating composition comprising a biodegradable carrier component and a biologically active component, the carrier component having a viscosity of from about 0.1 to about 15000 cP, or from about 0.1 to about 5000 cP. In yet another specific embodiment, the coated stent comprises a stent and a coating composition that comprises a biodegradable carrier component and a biologically active component, and the coating composition (or at least the carrier component thereof) is in a solid state outside of a human body and a liquid inside of a human body.

In another aspect, the invention can include a treatment method, comprising attaching a stent to a catheter, spraying the catheter and the stent with a coating composition comprising a biodegradable carrier component, and a biologically active component having a melting point of about 50° C. or less, and inserting the coated stent into a body lumen of a person.

In another aspect, the invention can include a coated stent, comprising a stent and a coating composition comprising a biologically active component and a biodegradable carrier component which may have a melting point of about 50° C. or less, and a catheter which can be coupled to the coated stent to form a treatment assembly.

BRIEF DESCRIPTION OF THE DRAWINGS

FIG. 3 is a stent.

FIG. 4 is a UV-VIS spectra of cerivastatin released from a stent coating.

FIG. 5 is a release profile of cerivastatin released from a stent coating.

FIG. 6 is a release profile of cerivastatin released from a stent coating.

DETAILED DESCRIPTION OF THE PREFERRED EMBODIMENT

Figure 1:
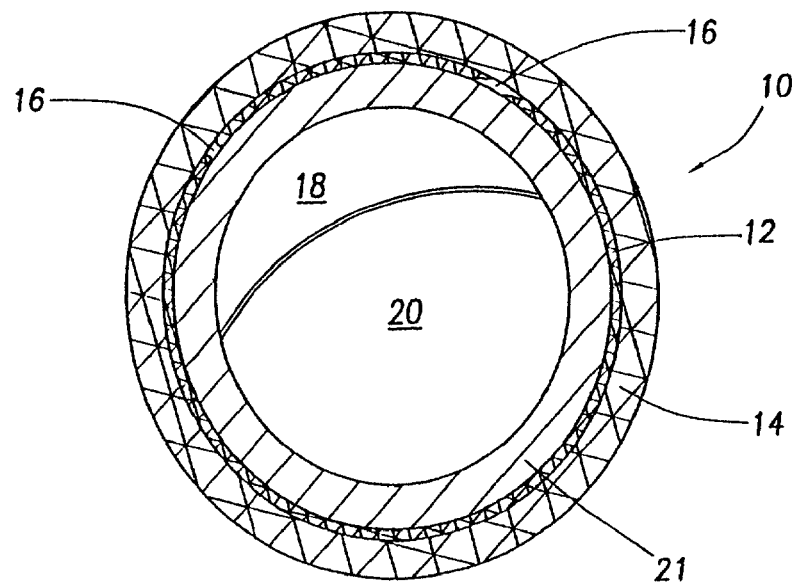
FIG. 1 is a cross-section of an artery experiencing restenosis in the presence of an uncoated stent.

An exemplary artery 10 experiencing restenosis is shown in FIG. 1. The endothelium 12 normally serves as a solid barrier between the layer of smooth muscle cells 14 and the arterial lumen 20. Small tears 16 in the endothelium 12 can expose smooth muscle cells 14, which can then migrate into the arterial lumen 20 and hyperproliferate into a mass 18 which can partially or completely occlude the lumen 20 even though an uncoated stent 21 is placed, during a procedure such as angioplasty, in the artery 10 to keep the arterial lumen 20 open.

Figure 2:
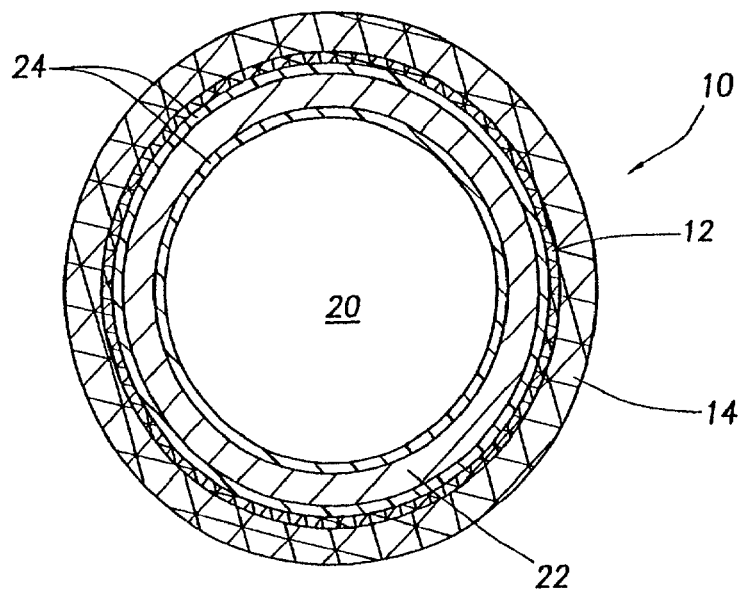
FIG. 2 is a cross-section of an artery containing a coated stent.

An artery 10 containing a coated stent 22 prepared according to an embodiment herein is shown in FIG. 2. The stent has a coating 24 containing a carrier and a bioactive compound which inhibits restenosis. By using a stent having this coating 24, the tears 16 shown in FIG. 1 in the endothelium 12 may be reduced or eliminated. Additionally, the mass 18 created by hyperproliferation of smooth muscle cells 14, as shown in FIG. 1, is eliminated or substantially reduced.

FIG. 3 illustrates a stent 21 suitable for use in connection with the present invention. In one embodiment, the stent 21 comprises a hollow reticulated tube. The tubular body of stent 21 is defined by a number of filaments or struts 25 which surround open cells 26. The stent 21 comprises an inner surface 27 facing the interior of the stent and an outer suface 28 facing the exterior. In a preferred embodiment, a coating (not shown) covers both the inner surface 27 and the outer surface 28. In alternative embodiments, the coating may cover only the inner surface, only the outer surface, or portions of one or both of the inner and outer surfaces. The coating may aggregate at the intersection of filaments 25. In a preferred embodiment, the coated stent 22 is made out of a metal or metal alloy, such as titanium, tantalum, stainless steel, or nitinol.

At least certain embodiments of the invention include a coated stent comprising a stent and a coating composition that includes a biologically active component and a biodegradable carrier component having a melting point of about 50° C. or less. Preferably, the biodegradable component has a melting point of from about 10° C. to about 50° C., and most preferably, from about 35° C. to about 45° C. In other specific embodiments, the invention provides a coated stent comprising a stent and a coating composition comprising a bioactive component and a liquid biodegradable carrier component that has a viscosity of from about 0.1 to about 15000 cP, and more preferably, from about 0.1 to about 5000 cP. In yet another specific embodiment, the invention includes a stent with a coating composition that is in a solid state at room temperature (22° C.) a human body and that melts to form a liquid inside a human body at body temperature (37° C.).

In a preferred embodiment, the coating 24 (FIG. 2) is made by mixing together a biologically active component (e.g., a restenosis-inhibiting agent) and a carrier in which the biologically active component is soluble. In a particularly preferred embodiment, the carrier is a liquid oil that adheres to the inner and outer surfaces 27, 28 of the stent 21 (FIG. 3). In other embodiments, the carrier comprises a low-melting polymer dissolved in a solvent, which is then removed by, e.g., drying, to yield a solid coating composition comprising the polymer and bioactive component, which may comprise a restenosis inhibiting agent such as an HMG-CoA reductase inhibitor.

As discussed, the coated stent of this invention includes a stent and a coating composition. The coating composition described herein is preferably a blend of a biologically active component and a biodegradable low-melting carrier component. The terms "biologically active" and "bioactive" refer to a substance having an effect on a living organism. See generally, Merriam Webster's Collegiate Dictionary ($10^{th}$ ed., 2001). Preferably, the effect of a bioactive compound is therapeutic in nature. The term "biodegradable" as used herein refers to a substance that breaks down into non-toxic byproducts which are eliminated by the body. The term "low-melting" refers to a composition having a melting point of 50° C. or less. Carrier compositions having melting points below 50° C. allow liquid-form delivery of a bioactive component to a body lumen either with no heat at all (because the composition is a liquid at body temperature) or with relatively benign heating without denaturing or other harm to the patient. In another embodiment, the coating composition is a blend of a bioactive component and a low-melting carrier comprising a biodegradable component, a biostable component, or both. In yet another embodiment, the coating composition is a liquid carrier that is biodegradable or biostable.

In addition to stents, examples of other medical devices that can be coated in accordance with aspects of the inventions disclosed herein include catheters, heart valves, pacemaker leads, annuloplasty rings and other medical implants. In other specific embodiments, coated angioplasty balloons and other coated medical devices can also comprise one of the coating compositions disclosed herein. However, stents are preferred. The coating composition may be applied to the stent (or other medical device) by any number of ways, e.g, by spraying the coating composition onto the stent, by immersing the stent in the coating composition, or by painting the stent with the coating composition. Preferably, a stent is coated in its expanded (i.e., enlarged diameter) form so that a sufficient amount of the coating composition will be applied to coat the entire surface of the expanded stent. When the stent is immersed in the coating composition, the excess coating composition on the surface of the stent may be removed, such as by brushing off the excess coating composition with a paint brush. In each of these coating applications, preferably both the outer and inner surfaces of the stent are coated.

An important aspect of the coating compositions of the present invention is the melting point of the biodegradable component. Preferably, the biodegradable component has a melting point of 50° C. or less, and more preferably from about 35° C. to about 45° C. The term "melting point" refers generally to the temperature at which a pure substance's crystals are in equilibrium with the liquid phase at atmospheric pressure. See generally, Hawley's Condensed Chemical Dictionary (11th Ed., 1987). Whenever melting points are discussed or referred to herein in quantitative terms, the melting point is measured according to differential scanning calorimetry or other standard methods shown in analytical or organic chemistry textbooks (see, e.g., Analytical Chemistry Handbook, Section 15, J. A. Dean, McGraw-Hill, Inc., 1995).

Another important aspect of certain embodiments of the invention is the biodegradable carrier component. In a preferred embodiment of this invention, the carrier component of the coating composition is or includes one or more non-polymeric, biodegradable compounds or materials, which either contain no polymers at all or contain essentially no polymers. For example, the carrier component should contain less than 50% by weight polymer, preferably less than 25 wt % polymer, more preferably less than 10 wt %, and most preferably less than 1 wt % polymer material. The biodegradable carrier component is preferably homogeneous (single phase) and may comprise a mixture of components that exist together as a solution, but which may alternatively be a multiple phase blend. Examples of preferred non-polymeric biodegradable carriers include liquid oleic acid, vitamin E, peanut oil, and cottonseed oil, which are liquids that are both hydrophobic and biocompatible. As used herein, the term "biocompatible" means any material that is not harmful to and preferably does not cause an immunological response in a living body, e.g., a living human being. As used herein, the term "polymer" means a macromolecule having recurring carbon-containing units, formed by a human-initiated or controlled polymerization reaction using monomers as reactants. The term "non-polymer" means any material that is not a polymer, including carbon-based materials such as naturally occurring oils.

Although non-polymeric carriers are preferred, the biodegradable carrier may also comprise a polymer. In one embodiment, the carrier comprises one or more biodegradable polymers, in which case it preferably consists essentially of one or more biodegradable polymers. In one embodiment, these polymers include low-melting polyhydroxy acids. Examples of polyhydroxy acids suitable for use in the present invention include poly-L-lactic acids, poly-DL-lactic acids, polyglycolic acids, polylactides including homopolymers and copolymers of lactides (including lactides made from all stereoisomers of lactic acids, such as D-,l-lactic acid and meso lactic acid), polylactones, polycaprolactones, polyglycolides, polypara-dioxanone, poly 1,4-dioxepan-2-one, poly 1,5-dioxepan-2-one, poly 6,6-dimethyl-1,4-dioxan-2-one, polyhydroxyvalerate, polyhydroxybutyrate, polytrimethylene carbonate, and blends of the foregoing, it being understood that the polymers have molecular weights such that their melting points are 50° C. or less. Polycaprolactones suitable for use in the present invention include low-melting, low molecular weight moieties of polycaprolactones such as poly(λ-caprolactone), polyvalerolactones such as polyδ-valerolactone), and polybutyrolactones such as poly(λ-butyrolactone). Other biodegradable polymers that can be used in carriers of the present invention are low-melting, low molecular weight moieties of polyanhydrides, polyphosphazenes, biodegradable polyamides such as synthetic polypeptides such as polylysine and polyaspartic acid, polyalkylene oxalates, polyorthoesters, polyphosphoesters, and polyorthocarbonates. The biodegradable polymers may be linear or branched. The biodegradable polymers may be homopolymers or terpolymers including random copolymers or block copolymers. Copolymers and blends of any of the listed polymers may be used. Polymer names above that are identical except for the presence or absence of parentheses represent the same polymers.

The structure and molecular weight of polymers used as biodegradable carriers in the present invention can be controlled during their synthesis in order to produce polymers that are liquid either at ambient temperatures (from 20° C. to 30° C.) or room temperature (about 22° C.) or that have low melting points. In a preferred embodiment, the melting point of the biodegradable polymers is above 30° C. but below typical human body temperature, i.e., 37° C. It is contemplated that a polymer with a melting point above 37° C. will not turn to liquid while or shortly after the stent is being inserted into the body. A biodegradable polymer having the desired melting point is preferably a polymer having a low molecular weight, e.g., a polymer having a molecular weight of less than about 2000 and preferably less than about 1000. High molecular weight polymers which are liquid at room temperature may also be used, however, such as certain polyorthoesters described in U.S. Pat. No. 4,913,903 which is hereby incorporated by reference herein in its entirety. Methods for making specific biodegradable polymers having the melting points, viscosities, and/or molecular weights described herein are known and will not be described herein. Conventional polymers having the desired melting points or viscosities can be obtained from Sigma-Aldrich. Examples of such polymers are shown in Table 1.

TABLE 1

Commercially available polymers (Sigma-Aldrich, St. Louis, MO) that can be used in coating applications

| Substance Name | Molecular weight (Dalton) | Melting point/softening point (° C.) | Physical appearance at ambient temperature |
|---|---|---|---|
| Polycaprolactone diol | 2000 | 50 | Solid |
| Polycaprolactone diol | 530 | 35 | Paste/waxy solid |
| Polycaprolactone triol | 900 | 30 | Paste/waxy solid |
| Polycaprolactone triol | 300 | 10 | Liquid |

As used herein, the terms "liquid" and "solid" are defined according to their broadest recognized definitions. Unless stated otherwise, a material is determined to be a "liquid" or "solid" at room temperature, i.e., 22° C. The term "liquid," when referring to carriers and coating compositions according to the present invention, includes a fluid (as water) that has no independent shape but has a definite volume, does not expand indefinitely and is only slightly compressible. The term "liquid" also includes any amorphous (e.g., noncrystalline) form of matter intermediate between gases and solids in which the molecules are much more highly concentrated than in gases but much less concentrated than in solids. See, generally, Hawley's Condensed Chemical Dictionary, (11th Ed., 1987). As discussed in further detail below, an amorphous liquid having a high viscosity can be used to advantage in compositions according to the present invention. The term "solid," when referring to carriers and coating compositions, includes a substance that does not flow perceptibly under moderate stress, has a definite capacity for resisting forces (e.g., compression or tension) which tend to deform it, and, under ordinary conditions, retains a definite size and shape. See generally, Merriam Webster's Collegiate Dictionary (10th ed., 2001).

The coating composition, including the bioactive component and the carrier, should be non-fragmentary. That is, the coating composition preferably does not break down into solid, potentially harmful fragments when the coated stent is in the body. In certain embodiments, the biodegradable carrier is a liquid when it is part of the coating composition residing on the stent outside the body. This liquid is incapable of breaking down into solid, potentially harmful fragments. In other embodiments, the biodegradable carrier is a solid that preferably becomes a liquid when introduced to the body (or shortly thereafter). For example, the carrier can be a solid at typical ambient temperatures (i.e., from 20° C. to 30° C.), and is preferably a solid at about 22° C., i.e., room temperature. It should, however, become a liquid at the temperature of a human body, which is approximately 37° C. In other words, the biodegradable component may be a solid outside a human body and a liquid inside a human body, so that it melts to form a liquid when inside the body. It is also contemplated that one skilled in the art may blend a biodegradable compound which is solid at typical ambient temperatures (or room temperature) with other components to form a carrier which can be either a liquid at ambient temperatures (or room temperature) or a liquid at the temperature of a human body.

In yet a further embodiment of the present invention the coating composition comprises a nonpolymeric compound that is a solid at room temperature but becomes a liquid at or near body temperature. In particular, the coating composition comprises low molecular weight waxes and derivatives having a melting point at between about 30° C. and 40° C., more particularly from about 35° C. to 40° C. and more particularly about 36° C. to about 38° C. In preferred embodiments, the low melting solid is applied to the stent by heating the solid to above its melting point, then sprayed, painted, dipped, molded, or otherwise applied to the stent as a liquid and allowing the liquid to resolidify upon cooling at ambient temperatures.

In another embodiment, two or more types of biodegradable compounds (polymers or non-polymers) may be blended together to obtain a liquid carrier for use in the coating composition. The biodegradable compounds can be liquids before they are mixed together, e.g., forming a homogeneous solution, mixture, or suspension. Alternatively, some of the biodegradable compounds may be solids before they are mixed with other liquid biodegradable compounds. The solid biodegradable compounds preferably dissolve when they are mixed with the liquid biodegradable compounds, resulting in a liquid carrier composition containing the different biodegradable compounds. In another embodiment, the biodegradable carrier component of the coating composition is a solid, which dissolves when mixed with the biologically active component and any other components included in the coating composition.

In certain specific embodiments, an important aspect of the biodegradable carrier component is its viscosity. Generally, viscosity is a term that refers to thickness or resistance to flow. In quantitative terms, the biodegradable component should have a viscosity of from about 0.1 to about 15000 cP. A person skilled in the polymer chemistry art can use Brookfield viscometer to measure viscosity of variety of fluids. Whenever viscosity is discussed herein in quantitative terms, the term "viscosity" is defined according to an ASTM method describing viscosity measurement can be found in Test Method D2983-87 entitled "Standard Test Method for Low-Temperature Viscosity of Automotive Fluid Lubricants Measured by Brookfield Viscometer."

Preferably, liquid stent coatings, such as those made from the materials described herein, have sufficient viscosity to withstand blood and other body fluids flowing against them without being washed off a stent, both during the insertion of the stent into the body and after the implantation of the stent at the desired site. Accordingly, in a preferred embodiment, the biodegradable carrier is a highly viscous liquid, e.g., an amorphous or even a "slimy" material that forms a liquid coating on the stent. A viscosity of from about 0.2 to about 200 cP is preferred. Preferably, the viscosity of the biodegradable carrier results in a coating that is less likely to be removed from the stent by the shear forces created by blood flow past the stent than a coating including a biodegradable carrier having a lower viscosity. The various viscosities discussed herein are measured at 20° C.

Biodegradable carriers and coating compositions according to the present invention are preferably hydrophobic so that the coating composition is not immediately dissolved and washed off the stent in the aqueous environment of the body. Hydrophilic and water-soluble biodegradable carriers and coating compositions may in some cases be used, but they are less preferred because of their tendency to be dissolved and washed off the stent more quickly than hydrophobic and water-insoluble biodegradable carriers and coating compositions. The term "hydrophobic" is defined according to its broadest recognized definition, and includes being antagonistic to water, and incapable of dissolving, or having limited solubility, in water. See generally, Hawley's Condensed Chemical Dictionary (11$^{th}$ Ed., 1987).

An important aspect of certain embodiments of the invention is the biologically active component. One or more biologically active components are included in the coating composition; preferably before the coating composition is applied to a stent. It is, however, contemplated that the biologically active component may in certain cases be combined with the carrier to form the coating composition after the biodegradable component is applied to the stent. As discussed above, the coated stent may be used to deliver a bioactive material to a localized area in a body. Preferably, the biologically active component is one that inhibits restenosis and/or prevents smooth muscle cell proliferation. Preferred examples of biologically active components are components that inhibit cell growth by affecting one of the steps involved in the cell cycle. Preferred components that affect the cell cycle are anticancer agents such as paclitaxel, immunosuppressant compounds such as rapamycin, antibiotics such as actinomycin D, and HMG-CoA reductase inhibitors such as cerivastatin. Other bioactive components forming part of the coating composition can include compounds such as antithrombin agents such as heparin and hirudin, calcium channel blockers such as colchicine, and compounds that promote endothelialization such as nitric oxide or nicotine. In a preferred embodiment, the biologically active component is hydrophobic and is easily dissolved in the biodegradable carrier to form a hydrophobic liquid coating composition. It is particularly preferred that the hydrophobic biologically active component(s) have a low molecular weight, i.e., a molecular weight below 2000, and more preferably below 1000, which can be used to administer a localized treatment in the area of stent deployment. The treatment may be for a condition such as restenosis.

In embodiments in which a biologically active component is included in the coating composition, the biologically active component itself may be a liquid. For example, vitamin E and nicotine (free base) are liquid at ambient temperatures (see Table 2) and may potentially have an anti-restenosis therapeutic effect. Preferably, the liquid biologically active component is biodegradable. In certain embodiments, the coating composition may consist essentially of the biologically active component, without a separate carrier component. In certain embodiments, the coating composition may consist of the biologically active component.

TABLE 2

Bioactive compounds that are liquid or low melting solids (Sigma-Aldrich 2000 catalog)

| Substance Name | Molecular weight (Dalton) | Molecular formula | Physical appearance at ambient temperature |
|---|---|---|---|
| Vitamin E | 431 | $C_{29}H_{50}O_2$ | Liquid |
| Vitamin E acetate | 473 | $C_{31}H_{52}O_3$ | Liquid |
| Nicotine | 162 | $C_{10}H_{14}N_2$ | Liquid |
| Nicotine Hemisulfate Salt | 212 | $C_{10}H_{14}N_2 \cdot 1/2H_2SO_4$ | Liquid |

As discussed above, the coating composition comprises a bioactive component and a biodegradable carrier component. Preferably, the coating composition comprises from 0.1% to 100% by weight of a biologically active component and from 1% to 99% by weight of a biodegradable carrier component. More preferably, the coating composition comprises from 0.1% to 50% by weight of a biologically active component and from 50% to 99.9% by weight of a biodegradable carrier component. The coating composition can be prepared in a number of ways including by simply mixing the bioactive component and the carrier component together to form a mixture, e.g., a solution or suspension. Alternatively, the bioactive component and the carrier component together are mixed in a suitable solvent, the coating is applied to the stent, and the solvent is removed. Preferably the coating composition is applied to the stent in its expanded state.

Where a biologically active component is included in or on the coating composition, the biologically active component may compromise an HMG-CoA reductase inhibitor. In certain specific embodiments, a coated stent can comprise a stent and a coating composition comprising a substantially unreacted HMG-CoA reductase inhibitor and a carrier. The carrier in the coating composition may be either biodegradable or biostable.

In one embodiment, the coating composition comprises a blend of an HMG-CoA reductase inhibitor and a liquid oil, which may be nonpolymeric or polymeric, capable of adhering to the inner surface 27 and/or the outer surface 28 of a stent 21 as shown in FIG. 3. In another embodiment, the coating composition comprises a blend of an HMG-CoA reductase inhibitor and a polymer. These two ingredients are preferably blended, e.g., mixed thoroughly but not chemically reacted to any substantial degree. Preferably the HMG-CoA reductase inhibitor is substantially unreacted. The term "substantially unreacted," when referring to the HMG-CoA reductase inhibitor, means that the inhibitor does not chemically react with the oil, the polymer or any other component of the coating or the stent, to any degree that substantially reduces its biological activity, such as inhibiting restenosis, e.g., by inhibiting the proliferation of smooth muscle cells 14. Where the coating comprises a polymer, the reductase inhibitor is preferably physically bound to the polymer and/or to the stent, but not chemically bound to any significant degree. In a preferred embodiment, the carrier, whether liquid or solid, polymeric or nonpolymeric, is incapable of reacting chemically with the inhibitor, i.e., is totally non-reactive (inert) with respect to the inhibitor.

The biologically active component, e.g., an HMG-CoA reductase inhibitor, should remain active even after being blended with the carrier to form the coating composition and after the coating composition is applied to the stent and the stent is sterilized. Further, the bioactive component preferably remains active when the coated stent is introduced into the body of a patient, e.g., through a lumen, remains active when it is released from the stent into the local environment. An "effective amount" of the HMG-CoA reductase inhibitor (or other bioactive component) means an amount that is sufficient when delivered to a localized area in the body lumen of a patient to inhibit the proliferation of smooth muscle cells in a body lumen of a patient. An "effective amount" of the biodegradable carrier means an amount of the carrier sufficient to dissolve or suspend an effective amount of the bioactive component and to substantially coat the portion of the stent that is desired to be coated, preferably the entire stent. Preferably, the carrier has no functional groups that react with the bioactive component, e.g., an HMG-CoA reductase inhibitor, under the conditions of forming the blend with the HMG-CoA reductase inhibitor.

In one or more embodiments, the carrier can be liquid at room temperature or it can be solid at room temperature but have a low melting point. It can alternatively or also have a specified high viscosity. In a specific embodiment, an HMG-CoA reductase inhibitor is provided in a nonpolymeric carrier. In another embodiment, the HMG-CoA reductase inhibitor is provided in a polymeric carrier, and the HMG-CoA reductase inhibitor may be physically bound to the polymer, chemically bound to the polymer, or both. The coating composition can be a liquid solution at room temperature, comprising the HMG-CoA reductase inhibitor and the polymeric or nonpolymeric carrier, and which may additionally comprise a solvent, which later may be removed, e.g., by drying. Alternatively, the coating composition may be a solid at room temperature and a liquid at body temperature.

In certain specific embodiments, the coating composition preferably includes an effective amount of an HMG-CoA reductase inhibitor. More particularly, the coating composition preferably includes an amount of an HMG-CoA reductase inhibitor that is sufficient to be therapeutically effective for inhibiting regrowth of plaque or inhibiting restenosis. In one embodiment, the coating composition may comprise from about 1 wt % to about 50 wt % HMG-CoA reductase inhibitor, based on the total weight of the coating composition. Preferably, the coating composition comprises from about 5 wt % to about 30 wt % HMG-CoA reductase inhibitor. More preferably, the coating composition includes from about 10 wt % to about 20 wt % HMG-CoA reductase inhibitor. Any HMG-CoA reductase inhibitor may be used, but the HMG-CoA reductase inhibitor is preferably hydrophobic and selected from the group consisting of cerivastatin, simvastatin, lovastatin, atorvastatin, and pravastatin. More preferably, the HMG-CoA reductase inhibitor is cerivastatin.

In one embodiment, the carrier of the coating composition is polymeric. In one embodiment, the coating composition comprises an effective amount of a polymer, e.g., an amount sufficient to both dissolve or suspend the HMG-CoA reductase inhibitor and coat a desired portion of the stent. The polymer is preferably non-reactive with the HMG-CoA reductase inhibitor, i.e., no chemical reaction occurs when the two are mixed. The polymer may be a polymer having no functional groups, or may be one having functional groups, but none that are reactive with the HMG-CoA reductase inhibitor. To provide coatings in which HMG-CoA reductase inhibitors are physically rather than chemically bound to the polymers in the coatings, HMG-CoA reductase inhibitors and carriers are chosen such that they will not have functional groups that will react with one another under the conditions of blending to form the coating solution. In coatings created by these methods, the HMG-CoA reductase inhibitors are preferably physically bound to the carrier but not chemically bound thereto. Accordingly, the chemical or molecular structure of the HMG-CoA reductase inhibitors is preferably unchanged when they are mixed with polymers to form the coatings. Therefore, when the HMG-CoA reductase inhibitors are released from these coatings, they remain in their desired active forms.

Liquid and low-melting polymers suitable for use as carriers in coating compositions according to the present invention may comprise a biodegradable polymer such as the biodegradable polymers discussed above. Alternatively, the low-melting polymer may comprise a biostable polymer, either alone or in combination with a biodegradable polymer. The term "biostable" is applied herein to any carrier, whether polymeric or nonpolymeric, and whether liquid or solid, that does not break down in the body. In preferred embodiments, biostable polymers that are preferred are biocompatible. Biostable low-melting polymers suitable for use in the present invention include, but are not limited to, silicone oils, prepolymers of polyurethanes, polyethylene glycol, polypropylene glycol, polyethylene, polybutadiene, prepolymers of polyurethanes, and other biostable liquids known in the art.

In a preferred embodiment, the polymer used to form the coating composition is low-melting polycaprolactone. Polycaprolactone is biocompatible, and it has a low glass transition temperature, which gives it flexibility and allows it to withstand the temperature changes stents often experience during their formation and use. For example, nitinol stents are preferably cooled to a temperature of about −50° C. so that they become flexible and can be compressed and fitted onto a catheter. A sheath placed over the stent (or another restraint such as a wire binding the ends of the stent, prevents the stent from expanding as it is introduced into a patient's body at a higher temperature. The sheath or other restraint is removed at the site of the stent's use, and the stent re-expands to the size at which it is coated with a composition that includes polycaprolactone. Polycaprolactone, unlike some other stent coating materials, does s not become brittle and crack throughout these fluctuations in stent temperature and size. Preferably, the polycaprolactone has a molecular weight between about 300 and 2,000. The polymer may be a linear, branched, graft or dendramer polymer. The polymer may have different functional end groups but a functional group that is non-reactive with the bioactive component such as an alkyl group is generally more preferred.

In one or more embodiments, the carrier may comprise more than one compound. The coating composition may further comprise both a liquid carrier and a solid carrier. In a still further aspect, the coating composition may also comprise a liquid carrier having more than one type of nonpolymeric or polymeric compound, and may further comprise both a polymeric material and a nonpolymeric material in the liquid carrier. The liquid carriers in the coating composition may be either biodegradable or biostable. Biodegradable polymers which can be used include those discussed above.

In a particularly preferred embodiment, the coating composition comprises a nonpolymeric liquid that remains a liquid after it is applied to the stent and the stent is deployed within the body of a patient, i.e., the coating liquid has a melting point below body temperature (37° C.), preferably below 30° C., more preferably below 20° C., still more preferably below 10° C. The liquid is preferably a viscous liquid that adheres to the at least a portion of the external surface 28 of the stent 22 in sufficient quantity to deliver a therapeutically effective amount of the bioactive component upon expansion in the body of the patient. In a preferred embodiment, the bioactive component is an HMG-CoA reductase inhibitor. Although the viscous liquid may be hydrophilic, in a preferred embodiment the viscous liquid is hydrophobic. Specifically, the carrier may comprise liquid Vitamin E and derivatives thereof, such as vitamin E acetate and vitamin E succinate. In another preferred embodiment, the viscous, hydrophobic liquid comprises a C4–C36 fatty acid or mixtures of such fatty acids, such as oleic acid or stearic acid, by way of nonlimiting example. In yet another preferred embodiment, the viscous, hydrophobic liquid comprises an oil. Exemplary oils suitable for use in the present invention include peanut oil, cottonseed oil, mineral oil, low molecular weight (C4–C36), and other viscous organic compounds that behave as oils such as, by way of nonlimiting example, 1,2 octanediol and other low molecular weight alcohols and polyols. Olive oil has a viscosity of 84 cP at 20° C. The viscosity of other materials is shown in Table 3 for reference purposes.

TABLE 3

Viscosity of various materials at 20° C.

| Substance Name | Viscosity (Centipoise) |
|---|---|
| Water | 1 |
| Caster oil | 986 |
| Nylon resin melt | 100000 |
| Diethyl ether | 0.23 |
| Olive oil | 84 |
| Benzene | 0.65 |

In a preferred embodiment, the HMG-CoA reductase inhibitor used as a bioactive component in the coating composition is cerivastatin. Cerivastatin is a very potent HMG-CoA reductase inhibitor. For example, when it is administered systemically, a therapeutic dose of cerivastatin is less than 1 mg per day, while other HMG-CoA reductase inhibitors must be administered in 50 mg doses. A thinner stent coating can be used if cerivastatin is the chosen HMG-CoA reductase inhibitor instead of other HMG-CoA reductase inhibitors because less of the bioactive coating is needed. For example, a stent coating preferably has a thickness of about 10–100 μm. If less drug and less carrier for that drug are required to inhibit restenosis, a stent coating having a thickness of 10–25 μm can be used. A thinner stent coating may be preferred because it leaves more of the arterial lumen open for blood flow. Thinner coatings are also useful in preserving sidebranch access in the case of coronary arteries. Sidebranches are small blood vessels that branch out from a coronary artery and provide blood to some part of the heart.

Cerivastatin has other desirable properties, in addition to its ability to inhibit the proliferation of smooth muscle cells that can contribute to restenosis. For example, cerivastatin has anti-thrombotic activity. Stents can often be sites of thrombus formation in the body because of the immunologically-triggered aggregation of different cell types and blood components at the site of a foreign object in the body. Including cerivastatin in a stent coating may help prevent thrombus formation at the site of the stent. Cerivastatin also promotes endothelialization, or the repair of the endothelium 12 after it is damaged, such as by the delivery and expansion of the stent in an artery or other body lumen. It is contemplated that the endothelialization triggered by cerivastatin can help repair the endothelium, and thus reduce tears in the endothelium through which smooth muscle cells and other cell types can migrate into the arterial lumen and proliferate, leading to restenosis.

As discussed above, other HMG-CoA reductase inhibitors may be used in these stent coatings. For example, fluvastatin, simvastatin, lovastatin, atorvastatin, and pravastatin may be used. While these compounds are known for their antihypercholesterolemic properties, it is believed that they may have other beneficial effects, such as restenosis inhibition or inhibition of smooth muscle cell proliferation, when they are delivered in a localized manner, such as from a stent coating.

In one embodiment, the coating compositions described herein may include more than one bioactive component, preferably more than onetype of HMG-CoA reductase inhibitor. For example, a coating composition may comprise cerivastatin and lovastatin. In other specific embodiments, the stent coatings described herein may comprise one or more drugs or bioactive compounds which inhibit restenosis and are not HMG-CoA reductase inhibitors. These drugs include, by way of nonlimiting example, rapamycin, paclitaxel, and actinomycin D. It is contemplated that combining another drug with an HMG-CoA reductase inhibitor may provide a more effective coating composition for inhibiting restenosis than a coating composition containing only one restenosis inhibiting agent.

Generally, the bioactive component is released from the stent by diffusion of the bioactive component from the carrier. If the carrier comprises a biodegradable polymer, the bioactive component is preferably released from the stent by the degradation of the polymer. A controlled release of the bioactive component from the coating can be achieved with a carrier comprising both a liquid and a solid through the relatively rapid release of the diffusion of the bioactive component from the liquid and a slower release from the solid. In a still further embodiment, a highly controlled delivery of the bioactive component can be achieved by a carrier comprising a liquid, a biodegradable (preferably solid) polymer, and a biostable (preferably solid) polymer. An initial release of the bioactive component from the liquid may be followed by a slower release from the biodegradable solid, and a still slower release from the biostable solid. The diffusion rate can be monitored and the dose of the HMG-CoA reductase inhibitor can be adjusted to deliver the drug at a desired rate. In one embodiment, a higher dose of a bioactive component can be delivered over a short period of time by using a liquid that releases a known amount of the inhibitor within one to three days. In another embodiment, a higher dose of a bioactive component can be delivered over a short period of time by using a nonpolymeric carrier such as vitamin E. In another embodiment, the bioactive component can be delivered via a biodegradable polymer that degrades within a few days, e.g., low molecular weight polyglycolic acid, releasing the bioactive component by both diffusion and/or coating degradation. In another embodiment, the carrier may comprise a nonpolymeric liquid and a biodegradable polymer that is a solid at room temperature and a liquid at body temperature.

Advantageously, the rate of release of a bioactive component from a liquid coating can be more easily predicted and is more consistent than the rate of release of a drug from other coatings in which the drug is chemically bound to the coating. With the coatings described herein, the bioactive component(s) are preferably physically released from the coatings, and thus not dependent on a chemical step, cleavage or hydrolysis, the rate for which could vary in different patients as well as within the same patient.

In at least certain embodiments the coating compositions of the present invention release their biologically active components in the body both by diffusion of the bioactive compounds from the coatings and by degradation of the coatings. For coating compositions that degrade within a few days or weeks in the body, much of the release of the biologically active components occurs in this time frame. This time-release feature is advantageous because it is believed that a high dose of a biologically active component, such as an anti-restenosis compound or an antibiotic, delivered quickly can often be more effective than a lower dose delivered over a longer period of time. For example, bacterial infections are often treated with high doses of antibiotics as soon as the infection is detected. A high initial dose of antibiotics may kill all of the bacteria, whereas a lower dose of antiobiotics administered over a longer period of time often results in the selection for, and survival of, bacteria that can survive in the presence of a low dose of the drug. Similarly, it is contemplated that if a low concentration of a biologically active component, such as a restenosis inhibitor which inhibits smooth muscle cell proliferation, is released slowly from a stent, some smooth muscle cells will still be able to proliferate and partially occlude the artery. Then, when the supply of the biologically active component is exhausted, this small group of smooth muscle cells will continue to proliferate and block a larger percentage of the arterial lumen. It is contemplated that this situation can be avoided or minimized using coating compositions described herein, because it is believed that the liquid coatings will be removed from the stent and degraded within a few days or weeks, and thus deliver a localized, high dose of a biologically active component in a short period of time.

The liquid coating compositions described herein which are made from biodegradable materials will degrade in the body and be removed from the angioplasty balloon or stent. When these coating compositions degrade, they typically degrade into their molecular subunits without creating fragments that may irritate or damage the endothelium and lead to restenosis, possibly in areas remote from the site of stent deployment. Thus, these coating compositions provide safe, temporary coatings for stents. Also, the coatings typically provide a smooth surface for stents, which minimizes abrasion or tearing damage to the endothelium by stents during and after their implantation in the body. It is contemplated that minimizing damage to the endothelium minimizes the likelihood of the development of restenosis. The coating compositions may also protect the stent itself from chemical or physical damage in the body The coatings of the present invention are suitable for use on any known cardiovascular stent such as, e.g., the Palmaz stent disclosed in U.S. Pat. Nos. 4,733,665 and 4,739,762. Other stents may also be used. Notwithstanding the foregoing, in a preferred embodiment, the coating compositions described herein are used on stents having struts, and further including a surface enhancing feature such as capillaries, grooves or channels in the struts, in which the coating composition can collect and be retained by surface tension.

The coating compositions described herein preferably remain on a stent, partially or in substantial part, after the stent has been introduced to the body, for at least several days and more preferably for several weeks. In one or more specific embodiments, the coating composition is a solid until it is placed in the body together with the stent, at which time it begins to melt to form a liquid, e.g., at 37° C. More preferably, the coating composition does not melt immediately upon insertion into the body, but melts upon reaching the site of its use.

As discussed above, one type of medical device suitable for use in connection with coatings of the present invention is an angioplasty balloon. The liquid coating compositions described herein preferably remain substantially intact on an angioplasty balloon during the insertion of the balloon through the body to the site of its use. Some of the coating composition will be transferred from the balloon to the hydrophobic plaque at the occluded site in the artery when the balloon is inflated at the site of an artery blockage. This is advantageous because the biologically active component in the coating composition will be directly transferred with the carrier onto the plaque. In this manner, the biologically active component can be delivered directly to its desired site of use. In a preferred embodiment, the coating compositions are hydrophobic. When hydrophobic coating compositions are used, they tend to dissolve faster than non-hydrophobic coating compositions after contacting the hydrophobic plaque and, thus, more readily release the biologically active component.

The coating composition comprising the carrier and the bioactive component can be applied to a stent in a number of different ways. Preferably, a stent is coated in its expanded form so that a sufficient amount of coating will be applied to completely coat the expanded stent. In a preferred embodiment, the coating composition is at least initially applied to the stent as a liquid. Spraying the stent with the liquid carrier results in a coating of uniform thickness on the struts of the stent. Where the coating composition comprises a polymer, the polymer is preferably dissolved in a suitable solvent to form a polymer solution and the stent is sprayed with the solution to provide the coating. Alternatively, the polymer solution may be painted on the stent or applied by other means known in the art, such as electrodeposition, dipping, casting or molding. In one embodiment, the stent may be dip coated or immersed in the solution, such that the solution completely coats the struts of the stent. In each of these coating applications, the entirety of both the outer and inner surfaces of the stent are preferably coated, although only portions of either or both surfaces may be coated in alternative embodiments. In one embodiment, excess coating composition is allowed to drain from the stent. In another embodiment, the solvent may then be dried to yield a solid coating composition having a melting point of 50° C. or less, preferably at body temperature or less. In a preferred embodiment, the stent is dried at from 20° C. to 30° C., preferably at room temperature, for a period of time sufficient to remove the solvent. The drying temperature should not be so high as to cause the polymer to react chemically with the HMG-CoA reductase inhibitor.

Generally, coating a stent by completely coating the struts of the stent is preferred. Complete coating typically provides uniform distribution of a drug along the surfaces of the stent. The top coating may be used to control the diffusion of the drug from the stent. The thickness of the coating is preferably 0.1 microns to 2 mm, more preferably from 1 to 100 microns, even more preferably from 1 to 25 microns. However, to provide additional coating to effect release of higher doses of the bioactive component, grooves, capillaries, channels or other depressions in the surface of the stent or struts may be provided to increase the surface area and thereby provide sites of enhanced adhesion of the coating.

As used herein, the term "solvent" is defined according to its broadest recognized definition and includes any material into which the carrier and/or the bioactive agent can dissolve, fully or partially, at room temperature or from 20° C. to 50° C. Methylene chloride is a preferred solvent for polymeric compositions. Methylene chloride's low boiling point facilitates removal from the polymer and the HMG-CoA reductase inhibitor at ambient temperatures by evaporation. However, it is contemplated that virtually any organic solvent that dissolves the polymer can be used. Solvents that can cause corrosion, such as highly acidic or basic aqueous solutions, are not preferred. Organic solvents that are biocompatible, have low boiling points and high flash points, are preferred. Other solvents that may be used include chloroform, toluene, cyclohexane, acetone, methylethyl ketone, ethyl formate, ethyl acetate, acetonitrile, n-methyl pyrrolidinone, dimethyl sulfoxide, n,n-dimethylacetamide, n,n-dimethyl formamide, ethanol, methanol, acetic acid, and supercritical carbon dioxide.

In another aspect, the invention can include a method of coating a stent. A specific embodiment of the method includes providing a stent, providing a coating composition comprising a biologically active component and a carrier component that has a melting point of about 50° C. or less, more preferably about 40° C. or less, most preferably body temperature (37° C.) or less, and applying the coating composition to the stent. In another embodiment, the invention includes a method that comprises providing a coating composition that includes a biologically active component and a liquid carrier component which has a viscosity of from about 0.1 to about 15000 cP, and applying the coating composition to the stent.

In a specific embodiment, the method of coating a stent comprises providing a stent, providing a coating composition comprising a blend of a substantially unreacted bioactive component and a polymeric or nonpolymeric carrier having a melting point of about 50° C. or less, and applying the coating composition to the stent. Providing to the coating composition may comprise mixing the bioactive component and a nonpolymeric liquid carrier. In one embodiment, the nonpolymeric liquid carrier comprises a C-6 to C-18 fatty acid, such as oleic acid or stearic acid. In another embodiment, the liquid carrier comprises a liquid selected from the group consisting of vitamin E, peanut oil, cottonseed oil, and mineral oil. In another embodiment, providing the coating composition may comprise mixing the bioactive compoent and a polymeric liquid carrier. In a further embodiment, providing the coating composition may include mixing an HMG-CoA reductase inhibitor, a low-melting polymer, and a solvent under conditions such that the HMG-CoA reductase inhibitor does not chemically react with the polymer, or does not react to any substantial extent, applying the mixture to the stent, and removing the solvent. Providing the coating composition may also include mixing the HMG-CoA reductase inhibitor, a polymer, and a solvent at a temperature of from about 20° C. to about 30° C., preferably at about 22° C. In another embodiment, providing a coating composition may include providing a solid coating comprising an HMG-CoA reductase inhibitor and a polymer.

In one or more specific embodiments, the invention can include a treatment method, comprising deploying a coated stent into a body lumen of a patient, the coated stent comprising a stent and a coating composition that comprises a carrier component and a bioactive component, the biodegradable component having a melting point of about 50° C. or less. In a preferred embodiment, the carrier is biodegradable, although biostable carriers may also be used. In other specific embodiments, the coated stent comprises a stent and a coating composition that includes a carrier component and a bioactive component, the carrier having a viscosity of from about 0.1 to about 15000. In yet another specific embodiment, the coated stent comprises a stent and a coating composition that includes a biodegradable carrier component and a bioactive component, and the carrier is in a solid state outside of a human body and a liquid inside of a human body.

In another aspect, the invention can include a treatment method comprising attaching a stent to a catheter, applying to the catheter and the stent a coating composition comprising a biodegradable carrier component having a melting point of about 50° C. or less and a bio active component, and deploying the coated stent into a body lumen of a patient.

In another aspect, the invention includes a method of treating an occluded artery comprising providing a stent, providing a coating composition comprising a low-melting nonpolymeric or polymeric carrier and a bioactive component in an amount effective to prevent or substantially reduce restenosis, applying the coating composition to the stent, and deploying the stent in the occluded artery at the site of occlusion. Providing a coating composition may comprise dissolving or suspending in a nonpolymeric liquid or low-melting carrier an amount of an HMG-CoA reductase inhibitor effective to prevent or substantially reduce restenosis. In another embodiment, providing a coating composition may comprise dissolving in a polymeric liquid or low-melting carrier an amount of an HMG-CoA reductase inhibitor effective to prevent or substantially reduce restenosis in an occluded vascular lumen. Where a polymeric carrier is provided, the HMG-CoA reductase inhibitor may be physically bound to the polymer, chemically bound to the polymer, or both. The coating composition may be a solution that comprises the HMG-CoA reductase inhibitor, the polymer, and a solvent. The solvent may be removed by, e.g., drying the stent or other methods known in the art. In another embodiment, the coating composition may comprise the HMG-CoA reductase inhibitor and a polymer having a melting point between 30° C. and 50° C., and applying the coating composition to the stent may comprise melting the coating composition, spraying the melted coating on the stent, and allowing the coating to solidify. The coating composition may include an amount of the HMG-CoA reductase inhibitor that is therapeutically effective for inhibiting regrowth of plaque or inhibiting restenosis. More particularly, the coating composition may comprise from about 1 wt % to about 50 wt % HMG-CoA reductase inhibitor, based on the total weight of the coating composition.

In another aspect, the invention can include a method of treating restenosis, comprising inserting a coated stent into a body lumen, the coated stent comprising a stent and a coating composition comprising a substantially unreacted HMG-CoA reductase inhibitor and a low-melting, nonpolymeric or polymeric carrier, which may be a liquid or a solid. In one embodiment, the coated stent releases the HMG-CoA reductase inhibitor in an amount sufficient to inhibit the proliferation of smooth muscle cells. In another embodiment, the coated stent releases the HMG-CoA reductase inhibitor in an amount sufficient to inhibit restenosis.

In another aspect, the invention may comprise a method of localized delivery of an HMG-CoA reductase inhibitor, comprising inserting a coated stent into a body lumen, the coated stent comprising a stent and a coating composition comprising a substantially unreacted HMG-CoA reductase inhibitor and a low-melting polymeric or nonpolymeric carrier. In one embodiment, the coated stent releases the HMG-CoA reductase inhibitor in an amount effective to inhibit the proliferation of smooth muscle cells. In another embodiment, the coated stent releases the HMG-CoA reductase inhibitor in an amount effective to inhibit restenosis.

In another aspect, the invention can include a coated stent, comprising a stent and a coating composition comprising a biologically active component and a biodegradable carrier component which may have a melting point of about 50° C. or less, and a catheter which can be coupled to the coated stent to form a treatment assembly.

In accordance with methods and compositions described herein, restenosis may be prevented or lessened using localized delivery of HMG-CoA reductase inhibitors from a liquid or low-melting carrier coupled to a stent placed in a body lumen. Preferably, metal stents are coated with a biocompatible coating composition comprising a carrier and an effective amount of an HMG-CoA reductase inhibitor. The coated stent can be deployed during any conventional percutaneous transluminal coronary angioplasty (PTCA) procedure. Controlled delivery from a stent of the active HMG-CoA reductase inhibitor, using a coating such as that described herein, in an effective amount, can inhibit the regrowth of plaque and prevent restenosis. While the stents shown and described in the various embodiments are vascular stents, any type of stent suitable for deployment in a body lumen of a patient may be used with the coatings described herein.

In certain specific embodiments of the coated stents and the methods described above, the coating compositions used may include more than one HMG-CoA reductase inhibitor or a restenosis inhibitor which is not an HMG-CoA reductase inhibitor. Preferably, these components are released from a stent in an amount effective to inhibit restenosis.

EXAMPLES

The following examples are included to demonstrate different illustrative embodiments or versions of the invention. However, those skilled in the art should, in light of the present disclosure, appreciate that many changes can be made in the specific embodiments which are disclosed and still obtain a like or similar result without departing from the spirit and scope of the invention.

Coronary stents were provided by Baylor Medical School and Sulzer Intratherapeutics. Poly(lactic acid)-co-poly(glycolic acid) (PLGA) polymer was purchased from Boehringer Ingelheim. Methylene chloride was purchased from Aldrich. Sulzer Carbomedics, Inc. provided medical grade silicone rubber.

Example 1

100 mg EVA (ethylene-vinyl acetate) polymer and 10 mg of cerivastatin were dissolved in 10 ml methylene chloride solution at room temperature. The solution was poured onto a glass plate and the solvent was allowed to evaporate for 12–24 hours. After almost complete removal of the solvent, the cerivastatin-loaded EVA film was removed from the glass plate and was cut to 1.5 cm by 1.5 cm size. The film was mounted on a Palmaz-Schatz coronary endovascular stent. Control EVA films were prepared in the following manner: 100 mg EVA polymer was dissolved in 10 ml methylene cloride solution at room temperature. The solution was poured onto a glass plate and the solvent was allowed to evaporate for 12–24 hours. After almost complete removal of the solvent, the control EVA film was removed from the glass plate and was cut to 1.5 cm by 1.5 cm size. The control film was mounted on a Palmaz-Schatz coronary endovascular stent. Release profiles were obtained for the coated stents.

Example 2

A 10% w/w solution of cerivastatin in vitamin E was created by the following method. Four (4) mg of cerivastatin was dissolved in one hundred (100) µl of methylene chloride. This solution was added to 36 mg of liquid vitamin E and mixed manually by stirring. The solution was allowed to stand at room temperature for one hour to enable the methylene chloride to evaporate from the solution. The resulting cerivastatin/vitamin E mixture was used to coat three "Protége" stents by simple surface application. Approximately 10–12 mg of vitamin E and drug was deposited on each stent.

Example 3

A coated stent prepared according to Examples 1 and 2 is immersed in an Eppendorf tube containing 1 ml phosphate buffered saline (PBS) and incubated on a rotator in a 37° C. oven. Buffer exchanges are performed at 1, 2, and 4 days following immersion in PBS. Collected samples are assayed for rifampin concentration using a UV-VIS spectrophotometer.

Example 4

A 50 ml round bottom flask with a Teflon coated magnetic stirrer is flame dried under repeated cycles of vacuum and dry nitrogen. Two (2) g trimethylol propane, 11.68 g D,L-lactide, and 0.20 mg stannous octoate are charged to the flask. The flask is then heated to 165° C. for 16 hours and then cooled. The liquid product is dissolved in 30 ml toluene and precipitated in large excess cold hexane. The precipitated polymer, which is a liquid at room temperature, is isolated and can be used in coating stents.

Example 5

Polycaprolactone diol (MW 2000) (PCL 2000) is purchased from Aldrich. This polymer melts at approximately 60–70° C., depending upon its thermal (cooling) history and the degree of crystallinity in the bulk polymer. This polymer is insoluble in water.

Example 6

Polycaprolactone triol (MW 300) (PCL 300) is purchased from Aldrich and used as received. This polymer is liquid at room temperature and is immiscible with water.

Example 7

One (1) g of PCL 300, a liquid at room temperature, and 50 mg of PCL 2000, a solid at room temperature, are mixed to obtain a viscous mixture which is liquid at room temperature. The viscosity of the mixture is greater than the viscosity of PCL 300.

Example 8

One (1) g PCL 300 (See Example 6) and 10 mg rifampin are added to a 2 ml glass vial. A 7×20 mm metal stent (Lot R0036203, Sulzer Intra Therapeutics) is added to the vial. The excess liquid on the surface of the stent is removed. The coated stent is then sterilized using ethylene oxide, compressed, and mounted on a balloon angioplasty catheter. It is then deployed at a diseased site in an artery using standard balloon angioplasty techniques and implanted at the site of reduced blood flow or obstruction of the artery. The hydrophobic liquid layer on the stent releases the drug in a controlled fashion.

Example 9

One (1) g PCL 300 (see Example 6) and 10 mg rifampin are added to a 2 ml glass vial. A paint brush is used to coat an angioplasty balloon surface with the PCL 300-rifampin mixture. The balloon is sterilized using ethylene oxide, compressed, and mounted on the balloon angioplasty catheter. It is then deployed at a diseased site in a coronary artery using standard balloon angioplasty technique. The coated balloon is expanded at the site of reduced blood flow or obstruction in the artery. The contact of the balloon surface with the arterial lumen wall transfers a portion of the liquid coating onto the wall surface as well as onto the material obstructing the arterial lumen. The hydrophobic liquid layer is transferred onto the lumen walls and onto the obstructing material, delivering the bioactive compound in a controlled manner.

Controlled release studies were done to determine the integrity and activity of cerivastatin released from stents coated with a solid polymer carrier and cerivastatin, and a vitamin E liquid carrier and cerivistatin. Stents coated according to the process of Examples 1 and 2 were immersed in an Eppendorf tube containing 1 ml phosphate buffered saline (PBS) and incubated on a rotator in a 37° C. oven. Buffer exchanges were performed at 1, 2, and 4 days following immersion in PBS. Collected samples were assayed for the spectral characteristics of cerivastatin using a UV-VIS spectrophotometer. Cerivastatin released from an EVA and cerivastatin coated stent such as the stent of Example 1 and pure cerivastatin in deionized water had almost identical UV-VIS spectra, as shown in FIG. 4, suggesting that the cerivastatin released from the stent was unaltered and thus remained biologically active.

The release of cerivastatin from stents coated according to the process of Example 1 was monitored over 7 days, as shown in FIG. 5. An EVA and cerivastatin coated stent such as the stent of Example 1 released >20 µg/ml cerivastatin per day (see FIG. 5), which is significantly higher than the 0.5 µg/ml concentration needed to inhibit proliferation of smooth muscle cells. Thus, stents produced according to this invention release a sufficient amount of cerivastatin to inhibit the proliferation of smooth muscle cells which occurs during restenosis.

The release of cerivastatin from stents coated with vitamin E according to the process of Example 2 was monitored over 11 days, as shown in FIG. 6. A liquid vitamin E and cerivastatin coated stent such as the stents of Example 2 released >20 µg/ml cerivastatin per day.

While the foregoing is directed to embodiments of the present invention, other and further embodiments of the invention may be devised without departing from the basic scope thereof, and the scope thereof is determined by the claims that follow, including equivalents.

What is claimed is:

1. A coated stent comprising a stent and a coating composition comprising a biologically active component and a nonpolymeric carrier component, the nonpolymeric carrier component selected from the group consisting of Vitamin E, Vitamin E acetate, Vitamin E succinate, oleic acid, peanut oil and cottonseed oil, and wherein the nonpolymeric carrier component has a melting point of about 50° C. or less and wherein the coating composition comprises the nonpolymeric carrier component by weight in the range from 50–99.9%.

2. The coated stent of claim 1, further comprising a catheter, wherein the catheter and the coated stent can be coupled to form a treatment assembly.

3. The coated stent of claim 1, wherein the carrier has a melting point of from about 35° C. to about 45° C.

4. The coated stent of claim 1 wherein the biologically active component has a melting point of about 50° C. or less.

5. A coated stent comprising a stent and a coating composition that includes a biologically active component and a nonpolymeric carrier, component wherein the nonpolymeric carrier component has a viscosity of from about 0.1 to about 15000 cP less and wherein the coating composition comprises a nonpolymeric carrier component by weight in the range from 50–99.9%.

6. A coated stent comprising a stent and a coating composition that includes a biologically active component and a nonpolymeric carrier, component, wherein the coating composition is in a solid state outside of a human body and melts to form a liquid inside of a human body.

7. The coated stent of claim 1 in which the coating composition is hydrophobic.

8. The coated stent of claim 1 in which the nonpolymeric carrier component is hydrophobic.

9. The coated stent of claim 1 in which the nonpolymeric carrier component is biodegradable.

10. The coated stent of claim 1 in which the biologically active component is capable of inhibiting restenosis.

11. The coated stent of claim 1 in which the biologically active component is selected from the group consisting of paclitaxel, actinomycin D, rapamycin, cerivastatin, fluvastatin, simvastatin, lovastatin, atorvastatin, and pravastatin.

12. The coated stent of claim 1, wherein the stent comprises struts and the struts comprise capillaries, grooves, and channels engraved in the struts.

13. The coated stent of claim 1, wherein the stent comprises a strut and the strut comprises a surface area enhancing feature.

14. The coated stent of claim 13, wherein the surface enhancing feature is selected from the group consisting of grooves, capillaries, or channels.

15. The coated stent of claim 14 wherein the surface enhancing feature contains at least some of the coating composition.

16. A method of coating a stent comprising:
providing a stent,
providing a coating composition comprising a biologically active component and a nonpolymeric carrier component having a melting point of about 50° C. or less, and wherein the coating composition comprises the nonpolymeric carrier component by weight in the range from 50–99.9%; and
applying the coating composition to the stent.

17. The method of claim 16, further comprising the step of expanding the stent to an increased diameter before applying the coating composition to the stent.

18. The method of claim 13, wherein applying the coating composition comprises spraying or painting the coating composition onto the stent, or immersing the stent in the coating composition.

19. A method of coating a stent comprising:
providing a stent,
providing a coating composition comprising a biologically active component and a nonpolymeric carrier component having a viscosity of from about 0.1 to about 15000 cP, and, wherein the coating composition comprises the nonpolymeric carrier component by weight in the range from 50–99.9%; and
applying the coating to the stent.

20. A method of treating restenosis comprising:
deploying a coated stent into a body lumen of a patient, the coated stent comprising a stent and a coating composition comprising a biologically active component and a nonpolymeric carrier having a melting point of about 50° C. or less and wherein the coating composition comprises the nonpolymeric carrier component by weight in the range from 50–99.9%.

21. A method of treating restenosis comprising:
deploying a coated stent into a body lumen of a patient, the coated stenting comprising a stent and a coating composition comprising a biologically active component and a nonpolymeric carrier component having a viscosity of from about 01. to about 15,000 cP and wherein the coating composition comprises the nonpolymeric carrier component by weight in the range from 50–99.9%.

22. A method of treating restenosis comprising:
providing a coated stent comprising a stent, a biologically active component and a coating composition comprising a nonpolymeric carrier component and wherein the coating composition comprises the nonpolymeric carrier component by weight in the range from 50–99.9%; and
deploying the coated stent into a body lumen of a patient, the coating composition changing from a solid to a liquid inside the patient.

23. A method of treating restenosis comprising:
coupling a stent to a catheter,
spraying the catheter and the stent with a coating composition comprising a biologically active component and a nonpolymeric carrier component having a melting point of about 50° C. or less, and
deploying the coated stent into a body lumen of a patient.

* * * * *

UNITED STATES PATENT AND TRADEMARK OFFICE
CERTIFICATE OF CORRECTION

PATENT NO. : 7,323,189 B2  
APPLICATION NO. : 10/027374  
DATED : January 29, 2008  
INVENTOR(S) : Chandrashekhar Pathak Page 1 of 1

It is certified that error appears in the above-identified patent and that said Letters Patent is hereby corrected as shown below:

Claim 5, Column 23, line 13, after "carrier", delete ",";
      Column 23, line 13, after "component", insert -- , --.

Claim 6, Column 23, line 20, after "carrier", delete ",".

Claim 18, Column 24, line 4, delete "13", and insert therefor -- 16 --.

Claim 20, Column 24, line 22, after "carrier", insert -- component --.

Signed and Sealed this

Thirteenth Day of May, 2008

JON W. DUDAS  
*Director of the United States Patent and Trademark Office*